United States Patent [19]

Egidio et al.

[11] Patent Number: 5,302,398
[45] Date of Patent: Apr. 12, 1994

[54] GASTRORESISTANT PHARMACEUTICAL FORMULATIONS FOR ORAL ADMINISTRATION CONTAINING SALTS OF BILE ACIDS

[75] Inventors: Marchi Egidio; Tamagnone Gianfranco, both of Casalecchio di Reno; Rotini L. Gabriele, Bologna, all of Italy

[73] Assignee: Alfa Wassermann S.p.A., Alanno Scalo, Italy

[21] Appl. No.: 861,461

[22] Filed: Apr. 1, 1992

[30] Foreign Application Priority Data

Apr. 12, 1991 [IT] Italy ................. 000112 A/91

[51] Int. Cl.$^5$ ................................. A61K 9/24
[52] U.S. Cl. ................. 424/474; 424/463; 424/472; 424/475; 424/480
[58] Field of Search .......... 424/456, 451, 457, 458, 424/459, 463, 464, 471, 472, 474, 475

[56] References Cited

U.S. PATENT DOCUMENTS

| | | | |
|---|---|---|---|
| 3,634,584 | 2/1969 | Poole | 424/471 |
| 4,432,966 | 2/1984 | Zeitoum et al. | 424/471 |
| 4,775,536 | 10/1988 | Patell | 424/471 |
| 4,891,223 | 1/1990 | Ambegaonkar et al. | 424/471 |
| 5,047,258 | 9/1991 | Belanger et al. | 424/471 |

OTHER PUBLICATIONS

Gennaro. (1985). Remington's Pharmaceutical Science, Mack. Pub., pp. 1636–1637.

Primary Examiner—Thurman K. Page
Assistant Examiner—Raj Bawa
Attorney, Agent, or Firm—Bucknam and Archer

[57] ABSTRACT

Pharmaceutical formulations for oral administration coated by an enterosoluble gastroresistant film, preferably selected from gastroresistant granulates, gastroresistant tablets, gastroresistant hard gelatine capsules containing powders or granulates or two or more tablets or oily suspensions, gastroresistant soft gelatine capsules containing oily suspensions and hard gelatine capsules containing gastroresistant granulates or two or more gastroresistant tablets, containing therapeutically effective amounts of salts of bile acids with alkali metals or organic bases, process for their preparation and therapeutic use thereof in the treatment of biliary calculoses, biliary dyspepsias, biliary cirrhosis and chronic and cholestatic hepatopathies.

5 Claims, No Drawings

GASTRORESISTANT PHARMACEUTICAL FORMULATIONS FOR ORAL ADMINISTRATION CONTAINING SALTS OF BILE ACIDS

BACKGROUND OF THE INVENTION

The therapeutic activities of some bile acids like, for instance, ursodeoxycholic, chenodeoxycholic, cholic and deoxycholic acids are well known for some time. In a first time their use has been addressed to the dissolution of the cholesterol gall-stones, by virtue of their ability of inhibiting the cholesterol synthesis, helping the cholesterol removal through the formation of mixed micelles and inhibiting the cholesterol absorption in the intestine. Subsequently the bile acids were used to treat biliary dyspepsias, biliary cirrhosis and chronic and cholestatic hepatopathies, as described in *Digestive Diseases*, 8, (1), 12-22, (1990) by Leuschner U. and Kurz W.

The oral therapy with bile acids is till now carried out by means of the administration of the acids in form of immediate or delayed release tablets or capsules. All these formulations exhibit the drawback of giving an incomplete absorption, due to a scarce bioavailability as clearly shown by Parquet M. et al., European Journal of Clinical Investigation, 15, (4), 171-8, (1985), Igimi H., Corey M.C., J. Lip. Res., 21, 72-90, (1980) and Roda A., Fini A., Hepatology, 4, 72-6, (1984).

This scarce bioavailability is due to the fact that bile acids, particularly ursodeoxycholic acid, dissolve very slowly in the intestine after having crossed unabsorbed and undissolved the stomach.

The water solubility of free bile acids, mainly that of ursodeoxycholic acid, is very low (53 $\mu$M) and, because of its restrained detergence (CMC = 14 mM). its solubility little increases with the increase of the pH and the complete solubilization takes place only at pH 8.47.

Therefore, ursodeoxycholic acid is completely solubilized and absorbed only when the intestinal pH exceeds the value of 8.4, while at lower values of pH a portion of ursodeoxycholic acid is not absorbed and undergoes a biotransformation to litocholic acid by means of the intestinal bacterial flora.

Therefore it is easily understandable why delayed release formulations containing urbodeoxycholic acid actually can have a lesser bioavailability than that of immediate release formulations in case the delayed release takes place in the intestinal zones where a greater metabolization contemporaneously occurs together with a greater solubilization.

Overcoming the problems of scarce absorption of the immediate or delayed release formulations containing bile acids used at present, is the object of the present invention. This scope is obtained by means of enterosoluble gastroresistant pharmaceutical formulations containing salts of bile acids with alkali metals or with organic bases.

The pharmaceutical formulations must be gastroresistant, because otherwise the strongly acid gastric juices would release the bile acids from their salts so that there would be again the problem of the slow and incomplete intestinal solubilization of the acids themselves, and must contain the salts of the bile acids so that they, once released in the intestine, can instantaneously be solubilized and immediate available for the absorption.

This object is achieved by the pharmaceutical formulation object of the present invention as it is clearly shown by biological tests of bioavailability carried out on men, by using a pharmaceutical formulation prepared according to the present invention in comparison with a commercial pharmaceutical formulation of ursodeoxycholic acid.

The experimental results showed a remarkable increase of the bioavailability of the formulation prepared according to the present invention in comparison with the commercial formulation. The average increase of the bioavailability (AUC) is equal to about 40%. Moreover the maximum hematic concentration (C max) reaches average values that are about three times higher and a quicker achievement of the maximum hematic peak (T max) is also noticed; in fact the formulation according to the present invention reached this peak in about 3 and half hours on the average while the commercial formulation reached it in about 4 hours and half.

These experimental data on men clearly show the full achievement of the objects of the invention and therefore the pharmaceutical formulations object of the present invention are perfectly suitable for the therapeutical uses of the bile acids, mainly for the treatment of biliary calculoses, biliary dyspepsias, biliary cirrhosis and chronic and cholestatic hepatopathies.

DETAILED DESCRIPTION OF THE INVENTION

Pharmaceutical formulations for oral use coated by an enterosoluble gastroresistant film containing therapeutically effective amounts of salts of bile acids with alkali metals or organic bases are the object of the present invention.

The process for preparing said pharmaceutical formulations and their therapeutic use in the treatment of biliary calculoses, biliary dyspepsias, biliary cirrhosis and chronic and cholestatic hepatopathies are further objects of the present invention.

Every kind of gastroresistant pharmaceutical formulations for oral use is suitable for the fulfillment of the present invention. Gastroresistant granulates, gastroresistant tablets, gastroresistant hard gelatine capsules containing powders or granulates or two or more tablets or oily suspensions, gastroresistant soft gelatine capsules containing oily suspensions and hard gelatine capsules containing gastroresistant granulates or two or more gastroresistant tablets, containing a therapeutically effective amount of salts of bile acids with alkali metals or organic based, are the preferred forms.

The distinctive feature of these pharmaceutical formulations resides is that they are coated by an enterosoluble gastroresistant film which allows the salts of the bile acids to cross the gastric juices unaltered and to be dissolved in the intestine where the absorption takes place. These pharmaceutical formulations contain an amount of said salts comprised between 50 and 750 mg and can be administered one or more times a day depending on the dosages and the individual therapeutic needs.

All the bile acids endowed with therapeutic activity can be advantageously used in the fulfillment of the present invention.

The cholic, deoxycholic, chenodeoxycholic, iocholic, iodeoxycholic and ursodeoxycholic acids are preferred in the realization of the present invention.

All the salts of the bile acids which show an adequate degree of solubility in aqueous medium or in a medium that simulates the intestinal fluid can be advantageously used in carrying out the present invention. The salts of the bile acids with alkali metals and with organic bases are preferred because of their solubility features. The salts of sodium, lithium, potassium, of tertiary aliphatic amines, like triethylamine, triethanolamine and trimethanolamine, of heterocyclic amines, like N-methyl-piperidine, piperazine, morpholine, N-methyl-morpholine and 1-(2-hydroxyethyl)pyrrolidine, of basic aminoacids like L-arginine, L-lysine and L-ornithine, of aminosugars like D-glucamine, N-methyl-D-glucamine and glucosamine and of quaternary ammonium derivatives like choline are preferred among them.

All the enterosoluble gastroresistant pharmaceutical formulations for oral use can be advantageously used in the realization of the present invention. The preferred formulations are the gastroresistant tablets, the gastroresistant, both hard and soft, capsules and the capsules containing two or more gastroresistant tablets. In this last case the gastroresistant film can be different for each kind of tablet so that each tablet can be solubilized in a different tract of the intestine in order to greatly aid the absorption of the drug.

Gastroresistant coatings that can be solubilized at pH values respectively higher than 5, 6 and 7, so that the solubilization takes place in an aimed way, were selected for carrying out the present invention.

The non-coated pharmaceutical forms are prepared according to known methods by using normal excipients, for instance binding agents like polyvinylpyrrolidone, carboxymethylcellulose, microgranular cellulose, lactose, saccharose or mannitol, disintegrating agents like reticulated polyvinylpyrrolidone, starches, sodium starch glycolate or alginates, lubricating agents like talc, magnesium stearate or stearic acid.

The non-coated pharmaceutical forms obtained according to known methods are transformed into the enterosoluble gastroresistant pharmaceutical formulations object of the present invention by means of a double coating.

The first coating, which is not protective, is carried out by using hydroxypropylmethylcellulose, polyethylene glycol 6000, titanium dioxide, talc and, optionally, pharmaceutically acceptable dyestuffs like, for instance, the iron oxides. This coating creates a film which acts as support for obtaining an optimal setting of the subsequent enterosoluble gastroresistant protective film on the pharmaceutical form. Many coating substances can be advantageously used to obtain an enterosoluble gastroresistant coating. Cellulose acetate, the copolymers of the methacrylic acid and of the methacrylic esters in different ratios, commercially known under the trademark EUDRAGIT ®, mainly EUDRAGIT ® L and EUDRAGIT ® S, polyvinylacetophthalate and hydroxypropylmethylcellulose phthalate.

Plasticizers, in an amount comprised between 5% and 15% in weight with respect to the amount of coating agent, are added for granting optimal flexibility and elasticity to the gastroresistant film.

Diethylphthalate, dibutylphthalate, triacetin, polyethylene glycols and acetylated monoglycerides are the plasticizers preferred in the realization of the present invention.

The process for preparing the pharmaceutical formulations object of the present invention comprises preparing according to known methods the various pharmaceutical forms for oral use not coated by the protective film. For instance the tablets are prepared by dry granulating the salt of the bile acid, by mixing it with the normal excipients like, for instance, reticulated polyvinylpyrrolidone, microgranular cellulose, magnesium stearate and talc and tabletting the resulting mixture.

The hard gelatine capsules can be filled either with a powder made by the sole active principle or by a mixture of the active principle together with one or more excipients, either with a granulate containing the active principle alone or together with one or more excipients, or with a suspension of the active principle in a suitable dispersing agent.

Afterwards the capsules are sealed, for instance, with an aqueous or hydroalcoholic solution of gelatine.

The soft gelatine capsules can be filled with a suspension of the active principle in a suitable dispersing agent and then they are sealed.

The tablets or the capsules, so obtained by means of known methods, are then submitted to the gastroprotection. A first, non-protective, coating, useful as support for obtaining an optimal setting of the protective enterosoluble gastroresistant film on the pharmaceutical form, is carried out before executing the coating by means of the enterosoluble gastroresistant film.

This non-protective coating is carried out by spraying on the pharmaceutical forms in coating pan a suspension made by hydroxypropylmethylcellulose, polyethylene glycol 6000, titanium dioxide, talc and, optionally, pharmaceutically acceptable dyestuffs like, for instance, the iron oxides, in a 22:1 mixture of ethyl alcohol and water. The weight of this first film is comprised between 1% and 5% of the weight of the non-coated pharmaceutical form.

The application of the enterosoluble gastroresistant film is carried out by solubilizing one or more coating substances together with one or more plasticizers in a solvent selected from methyl, ethyl or isopropyl alcohol, acetone or mixtures thereof with water and spraying this solution in coating pan on the pharmaceutical formulations previously coated by means of the non-protective coating, in such an amount that the weight of the enterosoluble gastroresistant film is comprised between 2% and 10% with respect to the weight of the non-coated pharmaceutical form.

The so obtained enterosoluble gastroresistant pharmaceutical formulations are able to release the salts of the bile acids in the intestine. In this way, the salts themselves, having the possibility of an immediate solubilization, are absorbed in a more quick and complete way from the intestinal tract as it is clearly shown by the experimental results of a pharmacokinetic test carried out on men.

One gastroresistant tablet according to the present invention, containing 475.2 mg of sodium salt of ursodeoxycholic acid and prepared according to the method described in example 4, was administered to each of 10 healthy persons, 5 men and 5 women, having a normal body weight, fasting for 8 hours. One week later the same persons were given, under the same circumstances, a tablet coming from a commercial pharmaceutical formulation containing 450 mg of ursodeoxycholic acid.

The hematic levels of ursodeoxycholic acid were evaluated for a period of time of 8 hours starting from the administration of the drug. They were evaluated by means of an immunoenzymatic method that uses specific antibodies for the free ursodeoxycholic acid prepared in New Zealand rabbits as described in articles of Roda A. et al. in Talanta, 31, 895, (1984) and in Analytical Biochemistry, 156, (2), 267–73, (1986).

The experimental results of the absorption during 8 hours, expressed as the area contained under the hematic curve (AUC), calculated as μmoles/lh, as the maximum hematic concentration that has been obtained (C max), expressed as μmoles/l, and as the time, expressed as hours, in which said maximum concentration has been obtained after the administration of the drug (T max), are reported in table 1.

TABLE 1

| | ABSORPTION TEST IN MAN | | | | | |
|---|---|---|---|---|---|---|
| | Sodium salt of ursodeoxycholic acid according to Example 4 | | | Commercial formulation of ursodeoxycholic acid | | |
| Person | AUC (μmoles/1/8h) | Cmax (μmoles/1) | Tmax (h) | AUC (μmoles/1/8h) | Cmax (μmoles/1) | Tmax (h) |
| 1 | 56.2 | 32 | 3 | 38.2 | 8 | 4 |
| 2 | 47.1 | 30 | 2.5 | 27.6 | 6 | 4.2 |
| 3 | 37.6 | 28 | 4 | 20.5 | 4 | 3.9 |
| 4 | 29.1 | 24 | 4 | 23.2 | 5 | 4.5 |
| 5 | 50.9 | 18 | 2.9 | 32.4 | 12 | 5.2 |
| 6 | 40.1 | 14 | 3.5 | 30.4 | 7 | 3.8 |
| 7 | 49.9 | 31 | 4 | 29.6 | 6 | 4.5 |
| 8 | 54.5 | 27 | 3.9 | 38.6 | 9 | 4.6 |
| 9 | 42.9 | 25 | 4.2 | 36.1 | 10 | 5.5 |
| 10 | 33.9 | 30 | 2.5 | 28.1 | 5 | 3.2 |
| | $\bar{x} \pm s.d.$ | $\bar{x} \pm s.d.$ | $\bar{x} \pm s.d.$ | $\bar{x} \pm s.d.$ | $\bar{x} \pm s.d.$ | $\bar{x} \pm s.d.$ |
| | 44.22 ± 8.56 | 25.90 ± 5.58 | 3.45 ± 0.63 | 30.47 ± 5.73 | 7.2 ± 2.4 | 4.34 ± 0.64 |

The experimental data reported in table 1 show that the absorption in man (expressed as AUC), by administering the same amount of the active principle, i.e. of ursodeoxycholic acid, increases of a value of about 40% for the pharmaceutical formulation according to example 4 in comparison with the commercial pharmaceutical formulation. Moreover the maximum hematic concentrations (C max) reached after the administration of the formulation described in example 4 are on the average three times higher than the maximum hematic concentrations reached after the administration of the commercial formulation. Lastly, also the speed of absorption is higher, because the reaching of the maximum hematic peak (T max) occurs, on the average, after about 3 and half hours after the treatment with the formulation according to example 4, i.e. about 1 hour before this reaching occurs with the commercial formulation of ursodeoxycholic acid.

Therefore the object of the present invention of producing oral pharmaceutical formulations containing a bile acid as the active principle and endowed with a better bioavailability in comparison with the pharmaceutical forms at present used, has been fully achieved.

Said oral gastroresistant pharmaceutical forms contain therapeutically effective amounts of salts of bile acids, preferably comprised between 50 and 750 mg, and can be administered one or more times a day, depending on the dosages and the individual therapeutic needs, in the treatment of biliary calculoses, biliary dyspepsias, biliary cirrhosis and chronic and cholestatic hepatopathies.

The salts of bile acids used in the realization of the present invention can be obtained in many and well known ways, for instance by salifying the bile acid in an aqueous or alcoholic medium with an organic or inorganic base followed by isolation by lyophilization or crystallization or precipitation with suitable solvents or evaporation of the solvent under vacuum.

The examples reported have to be considered only as a further illustration and not as a limitation of the invention.

EXAMPLE 1

LITHIUM SALT OF THE URSODEOXYCHOLIC ACID

A solution containing 3.92 g (10 mmoles) of ursodeoxycholic acid in 50 ml of ethyl alcohol is mixed under stirring with a solution containing 0.24 g (10 mmoles) of lithium hydroxide in 5 ml of distilled water and the mixture is evaporated under vacuum. The obtained solid is treated with ethyl ether and filtered obtaining with quantitative yield a white powder corresponding to the salt in object.

A 1% (w/v) aqueous solution of said salt shows a pH value equal to 8.13.

The sodium and potassium salts of the ursodeoxycholic acid, whose 1% (w/v) aqueous solutions show pH values respectively equal to 7.80 and 7.90, are prepared in a similar manner.

EXAMPLE 2

1-(2-HYDROXYETHYL)PYRROLIDINE SALT OF THE URSODEOXYCHOLIC ACID

20 Ml of a 0.5 M aqueous solution (10 mmoles) of 1-(2-hydroxyethyl)pyrrolidine are added under stirring to a suspension containing 3.92 g (10 mmoles) of ursodeoxycholic acid in 50 ml of water prolonging the stirring until complete solubilization. The obtained solution is then freeze-dried obtaining with quantitative yield a white powder corresponding to the salt in object. A 1% (w/v) aqueous solution of said salt shows a pH value equal to 7.90.

The N-methyl-D-glucamine and L-arginine salts of the ursodeoxycholic acid, whose 1% (w/v) aqueous solutions show pH values respectively equal to 8.06 and 7.75, are prepared in a similar manner.

EXAMPLE 3

CHOLINE SALT OF THE URSODEOXYCHOLIC ACID

10 Ml of a 1 M aqueous solution (10 mmoles) of choline bicarbonate are added under stirring to a suspension containing 3.92 g (10 mmoles) of ursodeoxycholic acid in 50 ml of water prolonging the stirring until complete solubilization. The obtained solution is then freeze-dried obtaining with quantitative yield a white powder corresponding to the salt in object A 1% (w/v) aqueous solution of said salt shows a pH value equal to 7.40.

EXAMPLE 4

GASTRORESISTANT TABLETS CONTAINING THE SODIUM SALT OF THE URSODEOXYCHOLIC ACID

| Composition of each tablet | |
|---|---|
| Sodium salt of the ursodeoxycholic acid | 475.2 mg |
| Reticulated polyvinylpyrrolidone | 21 mg |
| Microgranular cellulose | 210 mg |
| Magnesium stearate | 12 mg |
| Talc | 6 mg |
| Hydroxypropylmethylcellulose | 14 mg |
| Polyethylene glycol 6000 | 0.4 mg |
| Titanium dioxide | 3.2 mg |
| Talc | 3.2 mg |
| Hydroxypropylmethylcellulose phthalate | 32 mg |
| Acetylated monoglycerides | 3.2 mg |

The sodium salt of the ursodeoxycholic acid is dry compacted and granulated on a 0.8 mm sieve. The granulate is mixed for 15 minutes with reticulated polyvinylpyrrolidone, microgranular cellulose, magnesium stearate and talc and then the mixture is tabletted. The tablets are coated in coating pan first with a dispersion of hydroxypropylmethylcellulose. polyethylene glycol 6000, titanium dioxide and talc in a 22:1 mixture of ethyl alcohol and water and then with a solution of hydroxypropylmethylcellulose phthalate and acetylated monoglycerides in a 89:11 mixture of ethyl alcohol and water.

EXAMPLE 5

GASTRORESISTANT TABLETS CONTAINING THE SODIUM SALT OF THE CHENODEOXYCHOLIC ACID

| Composition of each tablet | |
|---|---|
| Sodium salt of the chenodeoxycholic acid | 316.8 mg |
| Reticulated Polyvinylpyrrolidone | 14 mg |
| Microgranular cellulose | 140 mg |
| Magnesium stearate | 8 mg |
| Talc | 4 mg |
| Hydroxypropylmethylcellulose | 10 mg |
| Polyethylene glycol 6000 | 0.3 mg |
| Titanium dioxide | 2.1 mg |
| Talc | 2.1 mg |
| Hydroxypropylmethylcellulose phthalate | 21 mg |
| Acetylated monoglycerides | 2.1 mg |

The tablets are prepared and coated according to the manner described in example 4.

EXAMPLE 6

GASTRORESISTANT TABLETS CONTAINING THE 1-(2-HYDROXYETHYL)PYRROLIDINE SALT OF THE URSODEOXYCHOLIC ACID

| Composition of the tablet | |
|---|---|
| 1-(2-Hydroxyethyl)pyrrolidine salt of the ursodeoxycholic acid | 582 mg |
| Reticulated polyvinylpyrrolidone | 21 mg |
| Microgranular cellulose | 210 mg |
| Magnesium stearate | 12 mg |
| Talc | 6 mg |
| Hydroxypropylmethylcellulose | 14 mg |
| Polyethylene glycol 6000 | 0.4 mg |
| Titanium dioxide | 3.2 mg |
| Talc | 3.2 mg |
| Hydroxypropylmethylcellulose phthalate | 32 mg |

| -continued | |
|---|---|
| Composition of the tablet | |
| Acetylated monoglycerides | 3.2 mg |

The tablets are prepared and coated according to the manner described in example 4.

EXAMPLE 7

GASTRORESISTANT TABLETS CONTAINING THE SODIUM SALT OF THE URSODEOXYCHOLIC AND CHENODEOXYCHOLIC ACIDS

| Composition of each tablet | |
|---|---|
| Sodium salt of ursodeoxycholic acid | 211.2 mg |
| Sodium salt of chenodeoxycholic acid | 264 mg |
| Reticulated polyvinylpyrrolidone | 21 mg |
| Microgranular cellulose | 210 mg |
| Magnesium stearate | 12 mg |
| Talc | 6 mg |
| Hydroxypropylmethylcellulose | 14 mg |
| Polyethylene glycol 6000 | 0.4 mg |
| Titanium dioxide | 3.2 mg |
| Talc | 3.2 mg |
| Hydroxypropylmethylcellulose phthalate | 32 mg |
| Acetylated monoglycerides | 3.2 mg |

The tablets are prepared and coated according to the manner described in example 4 using a mixture of the sodium salts of the ursodeoxycholic and of the chenodeoxycholic acids instead of the sodium salt of the ursodeoxycholic acid.

EXAMPLE 8

GASTRORESISTANT TABLETS CONTAINING THE SODIUM SALT OF THE URSODEOXYCHOLIC ACID

| Composition of each tablet | |
|---|---|
| Sodium salt of the ursodeoxycholic acid | 158.4 mg |
| Reticulated polyvinylpyrrolidone | 7 mg |
| Microgranular cellulose | 70 mg |
| Magnesium stearate | 4 mg |
| Talc | 2 mg |
| Hydroxypropylmethylcellulose | 4.7 mg |
| Polyethylene glycol 6000 | 0.13 mg |
| Titanium dioxide | 1.1 mg |
| Talc | 1.1 mg |
| Hydroxypropylmethylcellulose phthalate | 10.7 mg |
| Acetylated monolycerides | 1.1 mg |

The tablets are prepared and coated according to the manner described in example 4.

EXAMPLE 9

GASTRORESISTANT HARD GELATINE CAPSULES CONTAINING THE SODIUM SALT OF THE URSODEOXYCHOLIC ACID

| Composition of capsule | |
|---|---|
| Sodium salt of the ursodeoxycholic acid | 316.8 mg |
| Reticulated polyvinylpyrrolidone | 15 mg |
| Maize starch | 10 mg |
| Magnesium stearate | 10 mg |
| Talc | 7 mg |
| Hydroxypropylmethylcellulose | 5 mg |
| Polyethylene glycol 6000 | 0.2 mg |
| Titanium ioxide | 1.2 mg |
| Talc | 1.2 mg |

-continued

| Composition of capsule | |
|---|---|
| Eudragit ® L | 20.7 mg |
| Dibutylphthalate | 2 mg |

The sodium salt of the ursodeoxycholic acid is mixed with the maize starch for 30 minutes and then the mixture is dry compacted and granulated on a 1 mm sieve. The granulate is mixed for 15 minutes with reticulated polyvinylpyrrolidone, magnesium stearate and talc and the mixture is shared in hard gelatine capsules that are sealed with a 31% (w/v) aqueous solution of gelatine and then are coated in coating pan first with a dispersion of hydroxypropylmethylcellulose, polyethylene glycol 6000, titanium dioxide and talc in a 22:1 mixture of ethyl alcohol and water and then with a solution of Eudragit ® L and dibutylphthalate in isopropyl alcohol.

EXAMPLE 10

GASTRORESISTANT CAPSULES OF SOFT GELATINE CONTAINING THE SODIUM SALT OF THE URSODEOXYCHOLIC ACID

| Composition of each capsule | |
|---|---|
| Sodium salt of the ursodeoxycholic acid | 237.6 mg |
| Precipitated silica | 3 mg |
| Caprilo-capric qlycerides | 380 mg |
| Hydroxypropylmethylcellulose | 10.5 mg |
| Polyethylene glycol 6000 | 0.6 mg |
| Titanium dioxide | 2.4 mg |
| Talc | 2.4 mg |
| Hydroxypropylmethylcellulose phthalate | 24 mg |
| Acetylated monoglycerides | 2.4 mg |

A mixture of sodium salt of the ursodeoxycholic acid, precipitated silica and caprilo-capric glycerides is homogenized in a cylinder mill and then is shared in type 10 oval soft gelatine capsules. These capsules are first coated in coating pan with a first film made by a suspension of hydroxypropylmethylcellulose, polyethylene glycol 6000, titanium dioxide and talc in a 22:1 mixture of 95% ethyl alcohol and water. Subsequently an enterosoluble gastroresistant coating is carried out by sprying in coating pan a solution of hydroxypropylmethylcellulose phthalate and acetylated monoglycerides in a 80:1 mixture of ethyl alcohol and water on the capsules coated with the first film.

EXAMPLE 11

HARD GELATINE CAPSULES CONTAINING THREE GASTRORESISTANT TABLETS OF SODIUM SALT OF THE URSODEOXYCHOLIC ACID

| Composition of each non-protected tablet | |
|---|---|
| Sodium salt of the ursodeoxycholic acid | 158.4 mg |
| Reticulated polyvinylpyrrolidone | 7 mg |
| Microgranular cellulose | 55 mg |
| Magnesium stearate | 4 mg |
| Talc | 2 mg |

The sodium salt of the ursodeoxycholic acid is dry compacted and granulated on a 0.8 mm sieve. The granulate is mixed for 15 minutes with reticulated polyvinylpyrrolidone, microgranular cellulose, magnesium stearate and talc and then the mixture is tabletted. The obtained tablets are shared in three identical portions, each of which is submitted to a different kind of gastroprotection indicated by the letters A, B and C.

| Coating of each type A tablet | |
|---|---|
| Hydroxypropylmethylcellulose | 4.6 mg |
| Polyethylene glycol 6000 | 0.13 mg |
| Titanium dioxide | 1.06 mg |
| Talc | 1.06 mg |
| Hydroxypropylmethylcellulose phthalate | 10.6 mg |
| Acetylated monoglycerides | 1.06 mg |

The tablets are coated in coating pan first with a dispersion of hydroxypropylmethylcellulose, polyethylene glycol 6000, titanium dioxide and talc in a 22:1 mixture of ethyl alcohol and water and then with a solution of hydroxypropylmethylcellulose phthalate and acetylated monoglycerides in a 89:11 mixture of ethyl alcohol and water.

The gastroprotected tablets of type A are solubilized at a pH value higher than 5.

| Coating of each type B tablet | |
|---|---|
| Hydroxypropylmethylcellulose | 4.6 mg |
| Polyethylene glycol 6000 | 0.13 mg |
| Titanium dioxide | 1.06 mg |
| Talc | 1.06 mg |
| Yellow iron oxide | 0.5 mg |
| Eudragit ® L | 10 mg |
| Dibutylphthalate | 1 mg |

The tablets are coated in coating pan first with a dispersion of hydroxypropylmethylcellulose, polyethylene glycol 6000, titanium dioxide, talc and yellow iron oxide in a 22:1 mixture of ethyl alcohol and water and then with a solution of Eudragit ® L and dibutylphthalate in isopropyl alcohol. The gastroprotected tablets of type B are solubilized at a pH value higher than 6.

| Coating of each type C tablet | |
|---|---|
| Hydroxypropylmethylcellulose | 4.6 mg |
| Polyethylene glycol 6000 | 0.13 mg |
| Titanium dioxide | 1.06 mg |
| Talc | 1.06 mg |
| Red iron oxide | 0.5 mg |
| Eudragit ® S | 10 mg |
| Dibutylphthalate | 1 mg |

The tablets are coated in coating pan first with a dispersion of hydroxypropylmethylcellulose, polyethylene glycol 6000, titanium dioxide, talc and red iron oxide in a 22:1 mixture of ethyl alcohol and water and then with a solution of Eudragit ® S and dibutylphthalate in isopropyl alcohol. The gastroprotected tablets of type C are solubilized at a pH value higher than 7.

The hard gelatine capsules are then filled with three gastroresistant tablets, one of each type A, B and C.

EXAMPLE 12

HARD GELATINE CAPSULES CONTAINING TWO GASTRORESISTANT TABLETS OF SODIUM SALT OF THE CHENODEOXYCHOLIC ACID

| Composition of each non-protected tablet | |
|---|---|
| Sodium salt of the chenodeoxycholic acid | 158.4 mg |
| Reticulated polyvinylpyrrolidone | 7 mg |
| Microgranular cellulose | 55 mg |

-continued

| Composition of each non-protected tablet | |
|---|---|
| Magnesium stearate | 4 mg |
| Talc | 2 mg |

The sodium salt of the chenodeoxycholic acid is dry compacted and granulated on a 0.8 mm sieve. The granulate is mixed for 15 minutes with reticulated polyvinylpyrrolidone, microgranular cellulose, magnesium stearate and talc and then the mixture is tabletted. The obtained tablets are divided in two identical portions, each of which is submitted to a different kind of gastroprotection indicated by the letters A and B.

| Coating of each type A tablet | |
|---|---|
| Hydroxypropylmethylcellulose | 4.6 mg |
| Polyethylene glycol 6000 | 0.13 mg |
| Titanium dioxide | 1.06 mg |
| Talc | 1.06 mg |
| Hydroxypropylmethylcellulose phthalate | 10.6 mg |
| Acetylated monoglycerides | 1.06 mg |

The tablets are coated as described for the type A tablets of example 11.

| Coating of each type B tablet | |
|---|---|
| Hydroxypropylmethylcellulose | 4.6 mg |
| Polyethylene glycol 6000 | 0.13 mg |
| Titanium dioxide | 1.06 mg |
| Talc | 1.06 mg |
| Red iron oxide | 0.5 mg |
| Eudragit ® S | 10 mg |
| Dibutylphthalate | 1 mg |

The tablets are coated as described for the type C tablets of example 11.

The hard gelatine capsules are then filled with a type A tablet and with a type B tablet.

EXAMPLE 13

HARD GELATINE CAPSULES CONTAINING TWO GASTRORESISTANT TABLETS OF THE LITHIUM SALT OF THE URSODEOXYCHOLIC ACID

The capsules are prepared as described in example 12 by using for each tablet 76.1 mg of the lithium salt of the ursodeoxycholic acid and an amount of excipients and coating agents equal to half of that described in example 12.

EXAMPLE 14

HARD GELATINE CAPSULES CONTAINING TWO GASTRORESISTANT TABLETS OF THE CHOLINE SALT OF THE URSODEOXYCHOLIC ACID

The capsules are prepared as described in example 12 by using for each tablet 94.9 mg of the choline salt of the ursodeoxycholic acid and an amount of excipients and coating agents equal to half of that described in example 12.

We claim:

1. A pharmaceutical formulation for oral use consisting of a core and an outer coating, said core containing a salt of a bile acid, said bile acid being a member selected from the group consisting of cholic, deoxycholic, chenodeoxycholic, iocholic, iodeoxycholic and ursodeoxycholic acids, said bile acid salt being a member selected from the group consisting of the salt with sodium, lithium, potassium, triethylamine, triethanolamine, trimethanolamine, N-methylmorpholine, 1-(2-hydroxyethyl)-pyrrolidine, L-arginine, L-lysine, L-ornithine, D-glucamine, N-methyl-D-glucamine, glucosamine and choline, the amount of said bile acid salt being 158–582 mgs, said outer coating is insoluble in the acidic gastric juice but is soluble at a pH higher than 5, said formulation containing between said core and said outer coating a non-protective coating in the amount of 1–5% by weight with respect to said non-coated portion, said non-protective coating consisting of hydroxypropylmethylcellulose, polyethylene glycol 6000, titanium dioxide and talc.

2. The formulation according to claim 1 wherein said outer coating is made by coating said core with at least one substance which is a member selected from the group consisting of cellulose acetate, copolymers of methacrylic acid and of methacrylic esters in different ratios, polyvinylacetophthalate and hydroxypropylmethyl-cellulose phthalate and a plasticizer which is at least one member selected from the group consisting of diethylphthalate, dibutylphthalate, triacetin, polyethylene glycols and acetylated monoglycerides, said outer coating being in amount between 2% and 10% of the weight of said core.

3. A pharmaceutical formulation for oral use consisting of a core and an outer coating said core containing a salt of a bile acid, said bile acid being a member selected from the group consisting of cholic, deoxycholic, chenodeoxycholic, iocholic, iodeoxycholic and ursodeoxycholic acids, said bile acid salt being a member selected from the group consisting of the salt with sodium, lithium, potassium, triethylamine, triethanolamine, trimethanolamine, N-methylmorpholine, 1-(2-hydroxyethyl)-pyrrolidine, L-arginine, L-lysine, L-ornithine, D-glucamine, N-methyl-D-glucamine, glucosamine and choline, the amount of said bile acid salt being 158–582 mgs, said outer coating is insoluble in the acidic gastric juice but is soluble at a pH higher than 5, said formulation containing between said core and said outer coating a non-protective coating in the amount of 1–5% by weight with respect to said non-coated portion, said non-protective coating consisting of at least one member selected from the group consisting of hydroxypropylmethyl-cellulose, polyethylene glycol 6000, titanium dioxide and talc wherein said non-protective coating additionally contains a pharmaceutically acceptable dye.

4. The formulation according to claim 1 which is a member selected from the group consisting of gastroresistant granulates, gastroresistant tablets, gastroresistant hard gelatine capsules containing powders or granulates or two or more tablets or oily suspensions, gastroresistant soft gelatine capsules containing oily suspensions and hard gelatine capsules containing gastroresistant granulates or two or more gastroresistant tablets.

5. The method of treatment of a living subject affected by biliary calculoses, biliary dyspepsias, biliary cirrhosis, chronic and cholestatic hepatopaties, which consists of orally administering to said subject a formulation for oral use consisting of a core and an outer coating, said core containing a bile acid salt, said bile acid being a member selected from the group consisting of cholic, deoxycholic, chenodeoxycholic, iocholic, iodexycholic and ursodeoxycholic acids and mixtures thereof, said salt of said bile acid being with an alkali metal or an organic base, the amount of said bile acid salt being 158–582 mgs and said outer coating is insoluble in the acidic gastric juice but is soluble at a pH higher than 5, said formulation having a non-protective coating between said core and said outer coating.

* * * * *